US010688036B2

(12) United States Patent
Ran et al.

(10) Patent No.: US 10,688,036 B2
(45) Date of Patent: Jun. 23, 2020

(54) PERSONAL CARE COMPOSITION

(71) Applicant: Conopco, Inc., Englewood Cliffs, NJ (US)

(72) Inventors: Li Ran, Shanghai (CN); Su Yuan, Shanghai (CN); Qiqing Zhang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 170 days.

(21) Appl. No.: 15/303,020

(22) PCT Filed: Mar. 23, 2015

(86) PCT No.: PCT/EP2015/056067
§ 371 (c)(1),
(2) Date: Oct. 10, 2016

(87) PCT Pub. No.: WO2015/158499
PCT Pub. Date: Oct. 22, 2015

(65) Prior Publication Data
US 2017/0027851 A1 Feb. 2, 2017

(30) Foreign Application Priority Data

Apr. 14, 2014 (WO) ................. PCT/CN2014/075300
Jun. 2, 2014 (EP) ..................................... 14170746

(51) Int. Cl.
*A61K 8/25* (2006.01)
*A61K 8/898* (2006.01)
*A61K 8/34* (2006.01)
*A61Q 13/00* (2006.01)
*A61K 8/73* (2006.01)
*A61Q 17/00* (2006.01)
*A61Q 17/04* (2006.01)
*A61Q 19/02* (2006.01)
*A61Q 19/08* (2006.01)
*A61K 8/06* (2006.01)

(52) U.S. Cl.
CPC .............. *A61K 8/898* (2013.01); *A61K 8/062* (2013.01); *A61K 8/25* (2013.01); *A61K 8/34* (2013.01); *A61K 8/345* (2013.01); *A61K 8/347* (2013.01); *A61K 8/732* (2013.01); *A61Q 13/00* (2013.01); *A61Q 17/005* (2013.01); *A61Q 17/04* (2013.01); *A61Q 19/02* (2013.01); *A61Q 19/08* (2013.01); *A61K 2800/612* (2013.01); *A61K 2800/77* (2013.01); *A61K 2800/805* (2013.01)

(58) Field of Classification Search
CPC ....................................................... A61K 8/25
See application file for complete search history.

(56) References Cited

U.S. PATENT DOCUMENTS

| 4,294,728 | A | * | 10/1981 | Vanlerberghe | ......... | A61K 8/345 |
| | | | | | | 424/70.19 |
| 4,529,586 | A | * | 7/1985 | De Marco | .............. | A61K 8/416 |
| | | | | | | 424/70.122 |
| 4,668,509 | A | | 5/1987 | Vanlerberghe et al. | | |
| 5,188,822 | A | | 2/1993 | Viccaro et al. | | |
| 7,282,236 | B2 | | 10/2007 | Michael et al. | | |
| 7,731,094 | B2 | | 6/2010 | Phillips | | |
| 7,776,348 | B2 | | 8/2010 | Gardel et al. | | |
| 9,132,103 | B2 | | 9/2015 | Medepalli et al. | | |
| 10,005,110 | B2 | | 6/2018 | Delbrassinne et al. | | |
| 2005/0277768 | A1 | * | 12/2005 | Buwalda | .............. | B01J 13/0052 |
| | | | | | | 536/102 |
| 2006/0127345 | A1 | | 6/2006 | Hilvert | | |
| 2008/0057013 | A1 | | 3/2008 | McDermott et al. | | |
| 2008/0118591 | A1 | | 5/2008 | Natsch | | |
| 2009/0068136 | A1 | * | 3/2009 | Beumer | ................... | A61K 8/88 |
| | | | | | | 424/70.16 |
| 2009/0176676 | A1 | | 7/2009 | Hilvert et al. | | |
| 2011/0067720 | A1 | * | 3/2011 | Ranade | ..................... | A61K 8/11 |
| | | | | | | 132/202 |
| 2011/0081392 | A1 | | 7/2011 | de Arruda et al. | | |
| 2011/0223114 | A1 | | 9/2011 | Chakrabortty et al. | | |
| 2012/0141569 | A1 | | 6/2012 | Lee et al. | | |
| 2013/0079419 | A1 | | 3/2013 | Zhang et al. | | |
| 2013/0327364 | A1 | * | 12/2013 | Delbrassinne | ....... | C11D 3/0026 |
| | | | | | | 134/26 |
| 2014/0242134 | A1 | | 8/2014 | Khoshdel et al. | | |
| 2014/0294974 | A1 | | 10/2014 | Khoshdel et al. | | |

FOREIGN PATENT DOCUMENTS

| CN | 1336936 | 2/2002 |
| CN | 1471903 | 2/2004 |
| CN | 101076373 | 11/2007 |
| CN | 102186341 | 9/2011 |
| CN | 102510723 | 6/2012 |
| CN | 102525840 | 7/2012 |

(Continued)

OTHER PUBLICATIONS

Aluminum Starch Octenylsuccinate, International Cosmetic Ingredient Dictionary and Handbook, 2006, pp. 1-2; CTFA Monograph ID: 115; XP002725309, 11th Edition, No. 112.
IPRP2 in PCTEP2015055824, dated Mar. 18, 2016.
Search Report and Written Opinion in PCTEP2015055824, May 19, 2015.
Search Report and Written Opinion in EP14170746, dated Nov. 18, 2014.
Search Report and Written Opinion in EP14170747, dated Nov. 19, 2014.
Search Report and Written Opinion in PCTEP2015056067, dated Jul. 14, 2015.

(Continued)

*Primary Examiner* — Benjamin J Packard
(74) *Attorney, Agent, or Firm* — Edward A. Squillante, Jr.

(57) ABSTRACT

An oil-in-water personal care composition is disclosed which comprises hydrophobically modified particles selected from the group consisting of silica, metal oxide and mixtures thereof, amino functionalized silicone and hydrophobic starch.

20 Claims, No Drawings

(56) References Cited

FOREIGN PATENT DOCUMENTS

| CN | 102552101 | 7/2012 | | |
|---|---|---|---|---|
| CN | 102869338 | 1/2013 | | |
| CN | 103370406 | 10/2013 | | |
| DE | 102007016708 A1 * | 10/2008 | .............. | A61K 8/27 |
| WO | WO9619192 | 6/1996 | | |
| WO | WO9631188 | 10/1996 | | |
| WO | WO0042076 | 7/2000 | | |
| WO | WO2010046238 | 4/2010 | | |
| WO | WO2011036048 | 3/2011 | | |
| WO | WO2011137563 | 11/2011 | | |
| WO | WO2012077001 | 6/2012 | | |
| WO | WO2013064365 | 5/2013 | | |
| WO | WO2013064367 | 5/2013 | | |
| WO | WO2013064597 | 5/2013 | | |
| WO | WO2013064599 | 5/2013 | | |

OTHER PUBLICATIONS

Co-Pending U.S. Application, filed Oct. 10, 2016, entitled Personal Care Composition.
Common types of topical formulations; Dermweb.com; Feb. 13, 2018; pp. 1-2, accessed from =http://www.dermweb.com/therapy/common.htm on Feb. 13, 2018.

* cited by examiner

PERSONAL CARE COMPOSITION

TECHNICAL FIELD OF THE INVENTION

The invention is concerned with an oil-in-water personal care composition suitable for benefit agent delivery. Moreover, the present invention also relates to the process for manufacturing such personal care compositions.

BACKGROUND OF THE INVENTION

Benefit agents such as anti-microbial agents, perfume, sunscreen agents, anti-aging agents, skin lightening agents are commonly incorporated in personal care compositions and are delivered to the skin of the human body to improve the skin condition. Due to the high cost of most benefit agents, it is desired to improve the delivery efficiencies of benefit agents to maximize the effectiveness of such benefit agents.

However, it is difficult to achieve high delivery of benefit agents from personal care compositions with a water continuous phase especially rinse-off products such as shampoos. Small molecules of benefit agents may form micelle structure with surfactants that makes it difficult for them to be released but easier for them to be rinsed off during washing.

The present inventors have now recognized there is a need to develop an oil-in-water personal care composition that can provide enhanced delivery efficiency of benefit agents. It has been found that this need can be met by using a combination of hydrophobically modified particles, amino functionalized silicone and hydrophobic starch. Additionally, it is further found that the process for manufacturing such compositions also affects the benefit agent delivery efficiency.

SUMMARY OF THE INVENTION

In a first aspect, the present invention is concerned with an oil-in-water personal care composition comprising:
  a) hydrophobically modified particles selected from the group consisting of silica, metal oxide and mixtures thereof;
  b) amino functionalized silicone; and
  c) hydrophobic starch.

In a second aspect, the present invention is directed to a packaged personal care product comprising the personal care composition of the first aspect of this invention.

In a third aspect, the present invention is also directed to a process for manufacturing an oil-in-water personal care composition comprising hydrophobically modified particles selected from the group consisting of silica, metal oxide and mixtures thereof, amino functionalized silicone and hydrophobic starch, wherein the process comprises the steps of:
  a) premixing the hydrophobically modified particles selected from the group consisting of silica, metal oxide and mixtures thereof, the amino functionalized silicone and the hydrophobic starch; and
  b) mixing the premix with other ingredients to form the personal care composition.

In a fourth aspect, the present invention is concerned with a personal care composition obtainable and/or obtained by a process of the third aspect.

In a fifth aspect, the present invention is directed to a method of using the personal care composition of any embodiment of the first and the fourth aspects of this invention to provide enhanced benefit agent delivery.

All other aspects of the present invention will more readily become apparent upon considering the detailed description and examples which follow.

Except in the examples, or where otherwise explicitly indicated, all numbers in this description indicating amounts of material or conditions of reaction, physical properties of materials and/or use may optionally be understood as modified by the word "about".

All amounts are by weight of the final personal care composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION

It has been found that an oil-in-water personal care composition comprising hydrophobically modified particles, amino functionalized silicone and hydrophobic starch can provide enhanced delivery efficiency of benefit agent. It is further found that the process for manufacturing an oil-in-water personal care composition comprising hydrophobically modified particles selected from the group consisting of silica, metal oxide and mixtures thereof, amino functionalized silicone and hydrophobic starch also affects the benefit agent delivery efficiency.

Benefit agents as used herein means an active typically delivered to an external surface of the human body to enhance or improve a characteristic of the surface. For example, anti-microbial agents such as thymol, terpineol, eugenol and climbazole; sunscreen agent such as octyl methoxycinnamate, octocrylene, octyl salicylate, benzophenone-3 and avobenzone; anti-aging, wrinkle-reducing, skin lightening agents, anti-acne agents, and sebum reduction agents such as alpha-hydroxy acids and esters, beta-hydroxy acids and ester, polyhydroxy acids and esters, kojic acid and esters, ferulic acid and ferulate derivatives, vanillic acid and esters, dioic acids and esters, niacinamide, vitamin C and its derivatives, 12-hydroxystearic acid, retinol, retinal, retinyl esters, hydroquinone, t-butyl hydroquinone, mulberry extract, licorice extract, and resorcinol derivatives; perfume such as myrcene, dihydromyrcenol, citral, tagetone, cis-geranic acid, citronellic acid and cis-geranic acid nitrile.

The personal care composition of the present invention may comprise a single benefit agent or a mixture of two or more benefit agents. Typically, the benefit agent is present in an amount from 0.01 to 20%, more preferably from 0.03 to 15%, more preferably still from 0.05 to 10%, most preferably from 0.1 to 5% by total weight of the personal care composition and including all ranges subsumed therein.

Delivery efficiency as used herein means the ability to deliver benefit agents to an external surface of the human body through topical application.

The personal care composition of the invention is an oil-in-water emulsion. Generally the water content is from 10 to 90%, more preferably from 15 to 85%, most preferably from 20 to 80% based on the total weight of the personal care composition and including all ranges subsumed therein.

Hydrophobically Modified Particles

The only limitation with respect to the type of hydrophobically modified particles that may be used in this invention is that the same is suitable for use in a personal care composition by consumers. The hydrophobically modified particle includes silica, metal oxide or mixtures thereof. Preferably the hydrophobically modified particle is hydrophobically modified silica.

In a preferred embodiment, the hydrophobically modified silica comprises at least one of the following groups:

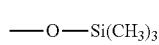
(I)

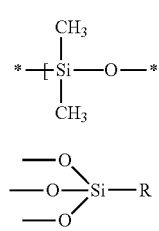
(II)

(III)

in which R is a $C_4$ to $C_{18}$ alkyl group, preferably R is a $C_8H_{17}$ alkyl group
or

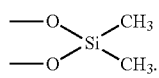
(IV)

Such silicas are described in U.S. Pat. No. 7,282,236 and made commercially available from suppliers like Evonik Degussa GmbH under the names Aerosil R805, R972, R 202, R812, R104, R816 and R711. Preferably, the silica particles comprise the group representing by formula III. More preferably, the silica particles comprise octylsilane (sold under the name Aerosil R805).

The hydrophobically modified particles according to the present invention can be of different sizes and shapes. Particle size, as used herein, refers to particle diameter unless otherwise stated. Diameter is meant to mean the largest measurable distance on a particle in the event a well-defined sphere is not generated. Particle size can be measured, for example, by dynamic light scattering (DLS). The size of hydrophobically modified particles is often from 1 nm to 100 nm, preferably from 3 nm to 70 nm, most preferably from 5 nm to 20 nm, including all ranges subsumed therein.

Typically, the personal care composition of the present invention comprises from 0.01 to 15% by weight of the hydrophobically modified particles, more preferably from 0.03 to 10%, most preferably from 0.05 to 5%, based on the total weight of the personal care composition and including all ranges subsumed therein.

Amino Functionalized Silicone

The personal care composition of this invention comprises an amino functionalized silicone. By "amino functionalized silicone" is meant a silicone containing at least one primary, secondary or tertiary amine group, or a quaternary ammonium group.

The primary, secondary, tertiary and/or quaternary amine groups may either form part of the main polymer chain or more preferably be carried by a side or pendant group carried by the polymeric backbone. Such polymers are described, for example, in U.S. Pat. No. 4,185,087.

In a preferred embodiment, the amino functionalized silicone has the general formula:

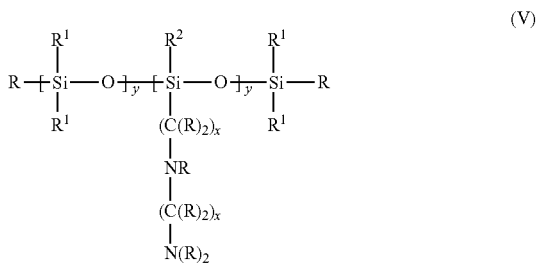
(V)

Where:
each R is independently H, OH, $OCH_3$ or $C_{1-4}$ alkyl;
each $R^1$ is independently OR, or a $C_{1-4}$ alkyl;
each $R^2$ is independently OR, or a $C_{1-4}$ alkyl; and
each x is independently an integer from 1 to 4 and each y is greater than zero and independently an integer to yield a polymer having a molecular weight from 500 to 1 million, and preferably, from 750 to 25,000, and most preferably from 1,000 to 15,000.

Other amino functionalized silicone suitable to use includes silicone cationic polymers represented by the formula:

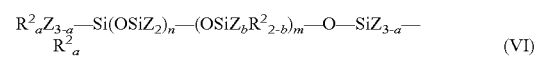
(VI)

where:
Z is hydrogen, phenyl, OH or a $C_1$-$C_{10}$ alkyl group;
each a is independently an integer from 0 to 3;
b is an integer from 0 to 1; and
m and n are integers whereby the sum of n+m ranges from 1 to 3,500, and preferably from 10 to 160;
each $R^2$ is independently a monovalent radical of formula —$C_qH_{2q}L$ where each q is independently a number from 2 to 10 and L is an amine or a quaternized amine represented by one of the following groups:
—$NR^3$—$CH_2$—$CH_2$—$N(R^3)_2$
—$N(R^3)_2$
—$N^{\oplus}(R^3)_3A^-$
—$N(R^3)$—$CH_2$—$CH_2$—$N^+R^3(H)_2A^-$,
where:
each $R^3$ is independently hydrogen, phenyl, benzyl or a $C_1$ to $C_{12}$ alkyl; and
each $A^-$ is independently fluoride, chloride, bromide or iodide anion.

Still other amino functionalized silicone suitable for use includes those having the formula (VII):

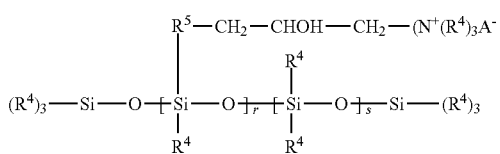

where:
- each $R^4$ is independently a $C_1$ to $C_{20}$ alkyl or $C_2$ to $C_{20}$ alkenyl;
- $R^5$ is a divalent $C_1$-$C_{18}$ group;
- $A^-$ is as previously defined;
- r is an integer from 2 to 20; and
- s is an integer from 15 to 75.

Preferably, the amino functionalized silicone has the INCI designation amodimethicone.

More preferably, amodimethicone is represented by formula (V) and made commercially available, for example, as DC 8500 by Dow Corning. It is also within the scope of this invention for the amino functionalized silicone to comprise trimethylsilylamodimethicone represented by formula (VI).

Typically, the personal care composition of the present invention comprises amino functionalized silicone in an amount from 0.01 to 20%, more preferably from 0.03 to 15%, more preferably still from 0.05 to 10%, most preferably from 0.1 to 5% by total weight of the personal care composition and including all ranges subsumed therein.

Preferably the weight ratio of hydrophobically modified particle to amino functionalized silicone is from 3:1 to 1:50, more preferably from 1:1 to 1:10.

Hydrophobic Starch

The personal care composition of the invention also comprises hydrophobic starch. Natural starches are usually modified physically or chemically to obtain modified starches. Physically modified starches include gelatinized starches, fully or partially hydrated starches and destructurized starches as well as crosslinked starches. Chemically modified varieties are those that have undergone, for example, acylation, alkylation, epoxidization, quaternization, carboxylation, phosphorylation, etherification (e.g. reaction with propylene or ethylene oxide), esterification (e.g. reaction with acetic anhydride). Generally, hydrophobic starch is starch which has been modified to impart hydrophobic groups that render the starch hydrophobic in nature. Preferably hydrophobic starches are starch esters containing hydrophobic groups and complex ethers of starch, for example, aluminium starch octenyl succinate.

The hydrophobic starch is generally present in personal care composition of this invention in an amount from 0.01 to 15%, more preferably from 0.03 to 10%, most preferably from 0.05 to 5%, based on the total weight of the personal care composition and including all ranges subsumed therein.

Other Ingredients

The personal care composition of the invention may be in any form including toners, lotions, creams, mousses, serum or gel that is suitable for topical application to the skin. The personal care composition can be either a leave-on or a rinse-off product, preferably a rinse-off product. In a preferred embodiment, the personal care composition of the invention is suitable for hair care, especially a rinse-off composition including shampoo and hair conditioner.

The personal care composition may contain one or more surfactants. The surfactant may be selected from the group consisting of anionic, non-ionic, cationic and amphoteric surfactants. Anionic surfactants are preferred. Usually anionic surfactants are selected from sodium lauryl sulphate and sodium lauryl ether sulphate(n)EO, (where n is from 1 to 3); preferably sodium lauryl ether sulphate(n)EO, (where n is from 1 to 3); most preferably sodium lauryl ether sulphate(n)EO where n=1.

The personal care composition may further contain co-surfactants such as amphoteric and zwitterionic surfactants. The most preferred co-surfactant is cocoamidopropyl betaine (CAPB).

Generally, the total amount of surfactant (including any co-surfactant) ranges from 0.5 to 45%, more preferably from 1.5 to 30%, most preferably from 5 to 20%, based on the total weight of the personal care composition and including all ranges subsumed therein.

The personal care composition may also contain conditioning actives including silicones, cationic deposition polymers, cationic surfactants, non-silicone oils or a mixture thereof. The amount of the conditioning actives in the personal care composition of this invention is preferably in the range from 0.05 to 15%, more preferably from 0.1 to 10%, most preferably from 0.5 to 8% based on the total weight of the personal care composition and including all ranges subsumed therein.

Thickener may also be used in this invention. Typical thickeners include cross-linked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include sclerotium, pectin and combinations of these gums. The amount of the thickener is preferably in the range from 0.0 to 5% by total weight of the personal care composition.

The personal care composition may further comprise other ingredients which are common in the art to enhance physical properties and performances. Suitable ingredients include but are not limited to emulsifiers, humectants, opacifiers, binders, colorants and pigments, pH adjusting agents, viscosity modifiers, preservatives, biological additives, buffering agents, natural extracts and essential oils.

In addition to water, organic solvent may also be included to act as co-solvent. Preferably the organic solvent is a polyhydric alcohol like glycerin (i.e. glycerol), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Preferably the polyhydric alcohol is propylene glycol.

Typically, the personal care composition of the present invention comprises co-solvent in an amount from 0.01 to 15%, more preferably from 0.03 to 10%, most preferably from 0.05 to 5%, based on the total weight of the personal care composition and including all ranges subsumed therein.

A wide variety of packaging can be employed to store and deliver the personal care compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered as a stick composition formulation in a container with propel-repel mechanism where the stick moves on a platform towards a dispensing orifice. Metallic cans pressurized by a propellant and having a spray nozzle serve as packaging for antiperspirants, shave creams and other sprayable personal care products. Toilet bars may have packaging constituted by a cellulosic or plastic wrapper or within a cardboard box or even encompassed by a shrink wrap plastic film.

Method for Manufacturing Personal Care Compositions

This invention is also directed to a method for manufacturing an oil-in-water personal care composition. Preferably, the method comprises the steps of:

a) premixing hydrophobically modified particles selected from the group consisting of silica, metal oxide and mixtures thereof, the amino functionalized silicone and hydrophobic starch; and b) mixing the premix with other ingredients to form the personal care composition.

Additionally or alternatively, the premix of step (a) comprises from 0.1 to 10% by weight of hydrophobically modified particles selected from the group consisting of silica, metal oxide and mixtures thereof.

Additionally or alternatively, the premix of step (a) comprises from 0.2 to 10% by weight of amino functionalized silicone.

In an especially preferred embodiment, the premix of step (a) comprises benefit agent.

Preferably the hydrophobic starch is present in an amount from 0.1 to 10% by total weight of the premix of step (a).

Additionally or alternatively, the premix of step (a) comprises from 0.3 to 10% by weight of benefit agent.

The invention is also concerned with the personal care composition obtainable and/or obtained by the method for manufacturing the personal care composition.

The invention is further concerned with a method of using the personal care composition to provide enhanced benefit agent delivery.

The following examples are provided to facilitate an understanding of the present invention. The examples are not provided to limit the scope of the claims.

EXAMPLES

Examples 1

A number of samples were made to demonstrate aspects of the present invention. The detailed formulations are outlined in Tables 1a and 1b. All ingredients are expressed by weight percent of the total formulation and as level of active ingredient.

TABLE 1a

| | | | Samples | | | | |
|---|---|---|---|---|---|---|---|
| Phase | Trade Name | INCI Name | 1 | 2 | 3 | 4 | 5 |
| A | SLES 1EO | Sodium Laureth Sulfate | 14 | 14 | 14 | 14 | 14 |
| | Dehyton KE | Cocoamidopropyl Betaine | 1.6 | 1.6 | 1.6 | 1.6 | 1.6 |
| | Jaguar C17 | Guar Hydroxypropyltrimonium chloride | 0.2 | 0.2 | 0.2 | 0.2 | 0.2 |
| | DC1788 | Silicones | 1.8 | 1.8 | 1.8 | 1.8 | 1.8 |
| | DC7123 | Silicones | 1.2 | 1.2 | 1.2 | 1.2 | 1.2 |
| | Carbopol 980 | Carbomer | 0.6 | 0.6 | 0.6 | 0.6 | 0.6 |
| | Perfume | Perfume | 0.75 | 0.75 | 0.75 | 0.75 | 0.75 |
| | NaOH | Sodium Hydroxide | 0.3 | 0.3 | 0.3 | 0.3 | 0.3 |
| | NaCl | Sodium Chloride | 0.5 | 0.5 | 0.5 | 0.5 | 0.5 |
| B | Thymol | 2-isopropyl-5-methylphenol | 0.2 | 0.2 | 0.2 | 0.2 | 0.2 |
| | Terpineol | 2-(4-Methyl-1-cyclohex-3-enyl)propan-2-ol | 0.5 | 0.5 | 0.5 | 0.5 | 0.5 |
| | Eugenol | 4-Allyl-2-methoxyphenol | 0.05 | 0.05 | 0.05 | 0.05 | 0.05 |
| | PG | Propylene Glycol | — | 0.15 | 0.15 | 0.15 | 0.15 |
| | Amino Si 8500 | Bis (C13-C15 Alkoxy) PG Amodimethicone | — | — | 0.47 | 0.47 | — |
| | Aerosil R805 | Hydrophobic silica | — | — | 0.15 | — | 0.15 |
| | Starch GFWP20 | Aluminum Starch Octenylsuccinate | 0.15 | 0.15 | 0.15 | 0.15 | 0.15 |
| C | Water and minors | | To 100 | To 100 | To 100 | To 100 | To 100 |

TABLE 1b

| | | | Samples | | | | |
|---|---|---|---|---|---|---|---|
| Phase | Trade Name | INCI Name | 6 | 7 | 8 | 9 | 10 |
| A | SLES 1EO | Sodium Laureth Sulfate | 14 | 14 | 14 | 14 | 14 |
| | Dehyton KE | Cocoamidopropyl Betaine | 1.6 | 1.6 | 1.6 | 1.6 | 1.6 |
| | Jaguar C17 | Guar Hydroxypropyltrimonium chloride | 0.2 | 0.2 | 0.2 | 0.2 | 0.2 |
| | DC1788 | Silicones | 1.8 | 1.8 | 1.8 | 1.8 | 1.8 |
| | DC7123 | Silicones | 1.2 | 1.2 | 1.2 | 1.2 | 1.2 |
| | Carbopol 980 | Carbomer | 0.6 | 0.6 | 0.6 | 0.6 | 0.6 |

TABLE 1b-continued

| Phase | Trade Name | INCI Name | Samples | | | | |
|---|---|---|---|---|---|---|---|
| | | | 6 | 7 | 8 | 9 | 10 |
| | Perfume | Perfume | 0.75 | 0.75 | 0.75 | 0.75 | 0.75 |
| | NaOH | Sodium Hydroxide | 0.3 | 0.3 | 0.3 | 0.3 | 0.3 |
| | NaCl | Sodium Chloride | 0.5 | 0.5 | 0.5 | 0.5 | 0.5 |
| B | Thymol | 2-isopropyl-5-methylphenol | 0.2 | 0.2 | — | 0.2 | 0.2 |
| | Terpineol | 2-(4-Methyl-1-cyclohex-3-enyl) propan-2-ol | 0.5 | 0.5 | — | 0.5 | 0.5 |
| | Eugenol | 4-Allyl-2-methoxyphenol | 0.05 | 0.05 | — | 0.05 | 0.05 |
| | PG | Propylene Glycol | — | 0.15 | 0.15 | — | 0.15 |
| | Amino Si 8500 | Bis (C13-C15 Alkoxy) PG Amodimethicone | 0.47 | 0.47 | 0.47 | 0.47 | 0.47 |
| | Aerosil R805 | Hydrophobic silica | 0.15 | 0.15 | 0.15 | 0.15 | 0.15 |
| | Starch GFWP20 | Aluminum Starch Octenylsuccinate | 0.15 | 0.15 | 0.15 | 0.15 | — |
| C | Water and minors | | To 100 | To 100 | To 100 | To 100 | To 100 |

Example 2

This example demonstrates the bio-efficacy of compositions using *Malassezia furfur* as the organism.

Formulation Process

For Phase A: SLES was first diluted to a solution of 26% activity and added into the main mixer. Carbopol 980 was diluted to a solution of 3% activity and added to mix with SLES for 15 minutes. NaOH diluted to a solution of 25% activity was added into the mixer and mixed for another 5 minutes, followed by the addition of Jaguar 017, DC1788, DC7123, perfume one by one. NaCl was added last to adjust the viscosity. The process was carried out under ambient temperature.

For Phase B: all the ingredients of Phase B were premixed to form a premix first then the resulting premix was dispersed into Phase A. The process was carried out under ambient (25° C.) temperature.

For Phase C: Phase C was added and mixed into the mixture of Phase A and B at last. The process was carried out under ambient (25° C.) temperature.

Assessment for Bio-Efficacy

The bio-efficacy was assessed using an in vitro substantivity assay which evaluates the effectiveness of actives in shampoo using *Malassezia furfur* as the organism. *Malassezia furfur* for the inoculation of artificial skin were initially grown in Pityrosporum Broth and then immediately added to 0.85 wt % sodium chloride prior to the inoculation of the Vitro-Skin™ (IMS inc) at a final concentration of 2-6×10$^5$ cells/mL. Vitro-Skin™ was sandwiched in a plastic ring support with its rough topography facing up. Testing sample was added to the plastic ring, followed by adding 1.8 mL water. The resulting solution mixture was stirred with a Teflon stirring rod before the solution was removed. The artificial skin was rinsed with distilled water with 30 seconds stirring before the rinsing water was removed. The water rinsing step was repeated once more before the plastic ring and Vitro-Skin™ was left to dry naturally. Vitro-Skin™ was placed onto a Modified Dixon Agar Plate (one skin per plate), and 0.2 mL 0.85 wt % sodium chloride with *Malassezia* was added gently onto the rough surface of the skin to form a film with a depth of 1-2 mm. The plates were then placed in an incubator (32° C.) for 24 h. After incubation, each piece of Vitro-Skin™ was carefully folded in half (inoculums on the inside) using sterile forceps, and placed into a vial containing 10 mL of Butterfield's phosphate buffer (pH 7.2), 0.1% Triton X-100, 0.5% Tween and 0.08% lecithin. The vial was vortexed for 1 minute and then treated ultrasonically for 1 minute. Then 20 µL of $10^0$-$10^{-3}$ dilutions were placed onto Modified Dixon Agar Plates, and incubated at 32° C. for 3-4 days. The number of colonies on each plate was counted, and the final numbers were determined by multiplying by the appropriate dilution.

In-vitro anti-fungal results against *malassezia* are shown in Table 2.

TABLE 2

| | Samples | | | | | | | | | |
|---|---|---|---|---|---|---|---|---|---|---|
| | 1 | 2 | 3 | 4 | 5 | 6 | 7 | 8 | 9 | 10 |
| Mean Log Reduction | 0.03 | −0.03 | −0.38 | −0.12 | −0.10 | −0.25 | −0.18 | −0.08 | −0.07 | 0.00 |
| Standard Deviation | 0.12 | 0.08 | 0.03 | 0.10 | 0.08 | 0.04 | 0.02 | 0.05 | 0.03 | 0.08 |

Sample 3, which is an embodiment of the present invention, demonstrates significantly better anti-fungal efficacy than Sample 2 which does not comprise hydrophobically modified particles and amino functionalized silicone.

Sample 4 and Sample 5 comprise either hydrophobically modified particles or amino functionalized silicone, both of which demonstrate lower anti-fungal efficacy compared to Sample 3.

Sample 10 comprising no hydrophobic starch showed greatly inferior anti-fungal efficacy to Sample 3.

Moreover, it is surprisingly found that the formulation process can have effect on the anti-fungal efficacy of the composition.

Samples 7 and 9 were prepared by adding ingredients of Phase B into Phase A one by one. All other samples were prepared by premixing all the ingredients of Phase B first to form a premix before dispersing the resulting premix into Phase A to obtain the final composition. Sample 3 exhibited superior anti-fungal efficacy to Sample 7, which indicates that premixing all the ingredients of Phase B to form a premix before adding them into Phase A is a preferred formulation process.

Example 3

This example demonstrates the stability of the composition.

Rheology Measurement Method

After storage at ambient and 50° C. for two weeks, the viscosity of the product was measured by DV-I+PRO Digital Viscometer (Brookfield Ltd) at a consistent shear rate of 20 rmp (RV-5). The values measured after 1 minute at a temperature of 30° C. are reported.

TABLE 3

| Sample | Viscosity after 2 weeks storage at ambient (mPa · s) | Viscosity after 2 weeks storage at 50° C. (mPa · s) |
| --- | --- | --- |
| 3 (without Phase B) | 5860 | 5600 |
| 3 | 5600 | 5640 |

Table 3 shows that the composition according to the present invention is stable.

Example 4

This example demonstrates the distribution of SS and TTE in localized areas of product microstructure.
SS: hydrophobically modified silica-amino functionalized silicone
TTE: thymol-terpineol-eugenol IR mappings and distributions of SS and TTE in the composition were performed on a NICOLET iN10 IR-microscope from Thermo Scientific. The cream-like samples were thin-spread on a gold coated plate and the absorbance data was collected on a reflection mode. When each IR mapping experiment was completed, characteristic IR peaks for SS and TTE were used to locate the distribution of SS and TTE in the selected area.

It is found that TTE is not evenly distributed and its distribution matches with the distribution of SS in Samples 3 and 6, while the distribution of TTE does not match with that of SS in other samples. The results indicate that SS structure may effectively entrap benefit agents that ensures the enhanced delivery of such agents.

The invention claimed is:

1. An oil-in-water personal care composition comprising:
    a) 0.01 to 15% by weight hydrophobically modified particles selected from the group consisting of silica, metal oxide and mixtures thereof;
    b) 0.01 to 15% by weight amino functionalized silicone;
    c) 0.01 to 15% by weight hydrophobic starch comprising aluminium starch octenyl succinate; and
    d) 0.1 to 20% by weight benefit agent comprising antimicrobial agent, the antimicrobial agent comprising thymol and terpineol, the personal care composition having anti-fungal efficacy against *Malassezia furfur*.

2. The personal care composition according to claim 1, wherein the personal care composition further comprises eugenol as a benefit agent.

3. The personal care composition according to claim 2, wherein the benefit agent further comprises perfume, sunscreen agents, anti-aging agents, skin lightening agents or mixtures thereof.

4. The personal care composition according to claim 1, wherein the benefit agent makes up from 0.1 to 5% by weight of the composition, and the composition is a shampoo.

5. The personal care composition according to claim 1, wherein the hydrophobically modified particle is hydrophobically modified silica.

6. The personal care composition according to claim 5, wherein the hydrophobically modified silica comprises:

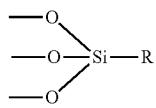

wherein R is a $C_4$ to $C_{18}$ alkyl group.

7. The personal care composition according to claim 1, wherein the amino functionalized silicone comprises amodimethicone.

8. The personal care composition according to claim 1, wherein the composition comprises amino functionalized silicone in an amount from 0.01 to 20%.

9. The personal care composition according to claim 1, wherein the weight ratio of hydrophobically modified particle to amino functionalized silicone is from 3:1 to 1:50.

10. The personal care composition according to claim 1, wherein the composition comprises hydrophobic starch in an amount from 0.01 to 15%.

11. The personal care composition according to claim 1, wherein the personal care composition further comprises a co-solvent, comprising propylene glycol.

12. The personal care composition according to claim 11, wherein the composition comprises co-solvent in an amount from 0.01 to 15%.

13. A process for manufacturing an oil-in-water personal care composition comprising hydrophobically modified particles selected from the group consisting of silica, metal oxide and mixtures thereof, amino functionalized silicone and hydrophobic starch, wherein the process comprises the steps of:
    a) premixing the hydrophobically modified particles selected from the group consisting of silica, metal oxide and mixtures thereof, the amino functionalized silicone and the hydrophobic starch to produce a premix; and
    b) mixing the premix with other ingredients to form the personal care composition, the other ingredients comprising thymol and terpineol, the composition comprising 0.01 to 20% by weight thymol and terpineol wherein the composition has anti-fungal efficacy against *Malassezia furfur*.

14. The process according to claim 13, wherein the premix of step (a) comprises from 0.1 to 10% by weight of hydrophobically modified particles selected from the group consisting of silica, metal oxide and mixtures thereof.

15. The process according to claim 13, wherein the premix of step (a) further comprises a benefit agent.

16. The personal care composition according to claim 6 wherein R is $C_8H_{17}$ alkyl group.

17. The personal care composition according to claim 1 wherein the composition is a rinse-off composition.

18. The personal care composition according to claim 1 wherein the composition is a leave-on composition.

19. The composition according to claim 1 wherein the amino functionalized silicone comprises trimethylsilylamodimethicone.

20. The composition according to claim 1 wherein the composition further comprises cocoamidopropyl betaine.

* * * * *